United States Patent [19]

Vanysacker

[11] Patent Number: 5,068,998

[45] Date of Patent: Dec. 3, 1991

[54] PROCESS FOR IMPROVING THE ORGANOLEPTIC PROPERTIES OF WINES

[75] Inventor: Yves Vanysacker, Mouscron, Belgium

[73] Assignee: Amchim S.A., Belgium

[21] Appl. No.: 404,542

[22] Filed: Sep. 8, 1989

Related U.S. Application Data

[63] Continuation-in-part of Ser. No. 168,013, Mar. 14, 1988, abandoned.

[30] Foreign Application Priority Data

Mar. 13, 1987 [FR] France .................. 87 03495

[51] Int. Cl.$^5$ .................. A01C 1/00; A01G 7/00; A01N 25/02
[52] U.S. Cl. .................. 47/58; 71/113; 71/122; 71/DIG. 1; 426/640
[58] Field of Search .................. 47/58; 426/308, 90, 426/102442, 640; 71/76, 92, Dig. 1, 113, 122

[56] References Cited

U.S. PATENT DOCUMENTS

| | | | |
|---|---|---|---|
| 3,220,823 | 11/1905 | Mihara et al. | 47/58 |
| 4,231,788 | 11/1980 | Siemer et al. | 71/113 |
| 4,433,002 | 2/1984 | Zilch | 426/442 |

FOREIGN PATENT DOCUMENTS 3532342  3/1987  Fed. Rep. of Germany ...... 426/640

OTHER PUBLICATIONS

Hart, H., et al. "Carboxylic Acids and Their Derivatives", 'Fats, Oils, Waxes and Detergents' Organic Chemistry (3rd Ed.) 1966 Houghton Miffin Co., Boston pp. 179–181;208–219.

Ponting, V. et al. "Temperature and Dipping Treatment Effects on Drying Rates and Drying Times of Grapes" *Food Technology*, Dec. 1970 pp. 85–88 (vol. 24).

Petrucci, V., et al. (1974) "Use of Oleic Acid Derivatives to Accelerate Drying of Thompson Seedless Grapes" J. Oil. Chem. Soc., vol. 51, No. 3,1974 pp. 77–80.

Bolin, H. R., et al. (1980) "Fatty Acid Esters and Carbonates in Grape Drying", J. Food Sci., vol. 45, No. 3, pp. 754–755.

Grncarevic, M., (1963) "Effect of Various Dipping Treatments on the Drying Rate of Grapes for Raisins" Amer. J. Entology and Viticulture vol. 14 pp. 230–234.

Anderson, W. P. "7 Formulations and Surfactants" *Weed Science:Principles* 1977 West Publishing Co., pp. 299–330.

The Feasibility of Using a Sprayed Oleic Acid Ester/Potassium Carbonate Mixture to Hasten the Maturity of Wine Grapes by Raymond Etherridge Watson, III, California State Univ. Fresno May 1981.

*Primary Examiner*—James R. Feyrer
*Attorney, Agent, or Firm*—Sughrue, Mion, Zinn Macpeak & Seas

[57] ABSTRACT

The present invention relates to a process for improving the organoleptic properties of wines comprising the step of treating standing grapes that will be used for wine production less than one month before harvest with a composition containing, as active ingredient, at least one anionic surface-active agent capable of rendering the cuticle of grapes hydrophilic, said composition being applied at a rate of about 5 to 50 liters per hectare.

The standing grapes are preferably sprayed with an aqueous suspension containing less than 20% by volume of a composition containing, as active ingredient, an alkali metal, preferably potassium, salt of an unsaturated fatty acid containing at least 16 and preferably 18 carbon atoms of an alkali metal, preferably posassium, salt of sulphate-containing fatty alcohols containing a significant proportion of $C_{16}$ to $C_{18}$ fatty alcohols or a sulphonated oil, such as an alkali metal sulphooleate of sulphoricinoleate.

18 Claims, No Drawings

PROCESS FOR IMPROVING THE ORGANOLEPTIC PROPERTIES OF WINES

This is a continuation-in-part of application No. 07/168,013 filed Mar. 14, 1988, now abandoned.

THE PRIOR ART

It is known that the cuticle of grapes is covered with a thin layer of wax which renders it hydrophobic and impermeable to water so that dehydration of the grape content is virtually impossible when the hygrometric level of the ambient air is low.

Inhibition of this dehydration prevents the content of the berries from being enriched in dry extract and consequently has an adverse effect on the sugar content of the grapes, inducing vine growers to chaptalize the wine producing musts in order to increase the alcohol content of the wine.

Petrucci et al in its article "Use of Oleic Acid derivatives to Accelerate Drying of Thompson Seedless Grapes" (Journal of The American Oil Chemists' Society—volume 51—pages 77 to 79—March 1984) disclose a method to accelerate drying for raisin production in Thompson seedless grapes that involved spraying a 2% emulsion of Emulsoyle (Ethylesters and emulsifiers) and potassium carbonate at a rate of 764 gal/acre followed by a second application of a 1% emulsion of Emulsoyle at a rate of 609 gal/acre, i.e. a total application of 241 liters/hectare.

A wine growner who reads the Petrucci et al reference sees that the on-the-vine treated grapes lost 53% moisture during the first five days. Such grapes are not suitable for making wines.

It is known that the priority aim of vinification techniques is to give wine a hygienic and nutrional value as high as possible while maintaining a satisfying flavor. Since the products responsible for the flavor and aroma are generally concentrated in the area of the cuticle, any technique that does not permit the migration of these products has to be prohibited, regardless of the convenience of such a technique (Larousse, La Grande Encyclopédie, 12634, col. 3 last paragraph and col. 4, first paragraph, 1976).

Moreover, it is well known for the skilled art worker a wine growner that spraying the vines with whatever chemical four weeks before the harvesting may cause tremendous damage to the wine (due to possible residues) even after some years. The most famous case is that of the Chevron Chemical Orthane applied on the Bordeaux Chateau Phelon-Segur where all the bottles of 1983 and 1984 have been returned to the owner.

For these reasons, the wine-grower will not treat the wine one month before harvest out of fear of causing tremendous damage to the wine.

The present invention has for object a process for improving the organoleptic properties of wines i.e. for increasing the content of the grapes in products responsible for the flavor and aroma which are generally concentrated in the area of the cuticle with respect to the sugar content of the grapes.

BRIEF DESCRIPTION OF THE INVENTION

It has now been found that it is surprisingly possible to improve the organoleptic properties of the wines obtained from these grapes by conventional wine production processes, by treating the standing grapes intended for wine production shortly before harvesting them.

This improvement in the organoleptic properties is manifested in liqueur-type or sweet wines as well as in dry wines.

This improvement in the organoleptic properties is accompanied by a significant increase in the alcohol content of the wines.

The present invention relates to a process for improving the organoleptic properties of wines comprising the step of treating standing grapes that will be used for wine production less than one month before harvest with a composition containing, as active ingredient, at least one anionic surface-active agent capable of rendering the cuticle of grapes hydrophilic, said composition being applied at a rate of about 5 to 50 liters per hectare.

In an embodiment of the process according to the invention, an aqueous suspension containing less than 20% by volume of a composition comprising at least one active ingredient is sprayed onto the standing grapes at a rate of about 5 to 50 liters per hectare, over a period of time ranging from approximately 5 to 20 days before the grape harvest.

In a preferred embodiment of the process according to the invention, an aqueous suspension containing about 10% by volume of a composition comprising at least one active ingredient is sprayed once at a rate of 20 to 40 liters per hectare.

The surface-active agent used in the process according to the invention may be an alkali metal salt, preferably potassium, of an unsaturated fatty acid containing at least 16, and preferably 18 carbon atoms, or an alkali metal salt, preferably potassium, of sulphate-containing fatty alcohols comprising a significant proportion of $C_{16}$ to $C_{18}$ alcohols, or a sulphonated oil such as alkali metal sulphooleate or sulphoricinoleate.

In the process according to the invention, the active ingredient of the composition used is advantageously a partially saponified edible oil, preferably vegetable oil, this oil preferably containing at least one unsaturated fatty acid or alcohol comprising at least 16 and preferably 18 carbon atoms.

The degree of saponification of the oil is advantageously between 10 and 70%, preferably between 20 and 40%.

The preferred partially saponified oil is an oil containing a significant, and preferably preponderant, quantity of oleic acid or alcohol.

An oil selected from olive, coconut, palm, safflower, soya, rapeseed, sunflower, corn, groundnut, almond, sesame and grape pip oil can be used as partially saponified vegetable oils.

The edible oil having a high content of long chain fatty acids which are partially saponified by an alkalimetal hydroxide such as NaOH, or preferably KOH, advantageously has added a small quantity of lower aliphatic alcohol, preferably ethanol or isopropanol.

In the composition used according to the invention, the active ingredient is advantageously formed by about 50 to 80, preferably 60 to 70 parts by weight of at least one edible oil comprising unsaturated fatty acids containing at least 16 carbon atoms which are saponified with about 5 to 25, preferably 10 to 20 parts by weight of potassium hydroxide, this oil having added about 5 to 30, preferably 15 to 25 parts by weight of ethanol.

EXAMPLES

The following examples illustrate, but do not limit, the preparation of compositions which can be used in the process according to the present invention.

Example 1: Concentrated composition 70 parts by weight of olive oil and 20 parts by weight of ethanol are mixed slowly at ambient temperature with 10 parts by weight of a 50% solution of KOH. The temperature rises to about 35° C. After 5 minutes, the reaction is completed and a clear concentrate is obtained.

Example 2: Concentrated composition 16 parts by weight of a 50% aqueous solution of KOH are added at ambient temperature to 74 parts by weight of coconut oil and 20 parts by weight of ethanol. The temperature reaches about 40° C. After stirring for 5 minutes, a clear concentrate is obtained.

Examples 3 to 6: Concentrated compositions

The method described in Example 1 is adopted, using palm oil, soya oil, corn oil and rape seed oil respectively. A clear concentrate is obtained in each case.

Example 7: Concentrated composition 70 parts by weight of oleic safflower oil containing about 80% of oleic acid are saponified with 8 parts by weight of a 50% KOH solution in the presence of isopropanol (about 15 parts by weight). A clear concentrate having a tendency to gel is obtained.

Examples 8 to 14: Dilute compositions ready for use

The concentrated compositions from Examples 1 to 7 are mixed with water in order to obtain suspensions containing about 10% of the concentrated compositions which can be used for spraying standing grapes.

TESTS

Tests carried out just before the grape harvest in 1984 and 1986 have demonstrated that the process according to the invention produces effects, the nature or the extent of which were surprising to a person skilled in the art.

These tests were carried out using a composition formed from 70 parts by weight of saponified olive oil per 10 parts by weight of potassium hydroxide, to which 20 parts by weight of ethanol were added. Said composition is called hereafter the above composition or the above-mentioned composition.

Tests No. 1

Tests were carried out by the l'Ecole de Viticulture et d'Oenologie de La Tour Blanche, Bommes 33210 Langon (France) in 1984 on a liqueur-type or sweet wine of the Sauterne region (Semillion vine).

The above-mentioned composition was sprayed onto three rows of vines in a plot on 8th Oct. 1984 in a dose of 40 liters per hectare.

The grapes from the control vines and the treated vines were harvested once on 18th Oct. 1984. Analysis of the must extracted from the control and treated grapes gave the results shown in Table I below:

TABLE I

|  | Control Grape Must | Treated Grape Must |
| --- | --- | --- |
| Sugars g/l | 234 | 290 |
| Alcohol potential % by volume | 13.7 | 17 |
| Total acidity g/l H$_2$SO$_4$ | 3.8 | 4.4 |
| Volume of juice collected hl/ha | 23 | 16.5 |

This table I demonstrates a slight increase in the total acidity of the treated grape must. This increase in acidity is considered by specialists to be particularly desirable for liqueur-type or sweet white wines.

Table I also shows a significant increase in the sugar content in the treated must as well as a significant increase (3.3% by volume) in the potential alcoholometric content of this must.

The musts were turned into wine and the wines were tasted and analysed.

The wine originating from the control grapes was aromatic but was disappointing in the mouth owing to its lack of character, whereas the wine originating from the treated grapes was pleasantly aromatic and palatable while remaining very pure.

Analysis of these wines has produced the results shown in Table II below:

TABLE II

|  | Wine from Control Grapes | Wine from Treated Grapes |
| --- | --- | --- |
| Total acidity g/l H$_2$SO$_4$ | 4.1 | 4.5 |
| Total dry extract g/l | 117.8 | 152.6 |
| Reduced dry extract g/l | 34.1 | 42.9 |
| Total alcohol % by volume | 16.9 | 19.2 |

The results shown in this Table II confirm the beneficial effects of the treatment according to the invention, in particular the surprising increase in the total acidity, considered as particularly beneficial for wines from the Sauterne region. The increase in the alcohol content of the wine obtained from the treated grape is also noteworthy.

Tests No. 2

Tests were carried out on grapes from the Sauvignon vine on plots having 6,600 vines per hectare. (Tests carried out by the Lycée Viticole d'Amboise).

The vines from the treated plots was sprayed with a dose of 40 liter per hectare of the above-mentioned composition.

The dates of the treatments and the harvest are indicated in Table III below:

TABLE III

| SAUVIGNON | Date of Treatment | Date of Harvest |
| --- | --- | --- |
| Vines | 19/9/86 | 29/9/86 |

Analysis of the control and treated grapes produced the results in Table IV below:

TABLE IV

| Vines | Alcohol potential in % by volume | Total acidity g/l H$_2$SO$_4$ |
| --- | --- | --- |
| Sauvignon | | |
| Control | 9.5 | 6.7 |
| Treated | 10.2 | 6.6 |

This table IV also demonstrates a substantial increase in the alcoholometric content and a slight reduction in the total acidity. It is seen that, in contrast to the expectations of the person skilled in the art, the significant increase in the alcoholometric content does not have an adverse effect on the acidity of the juice.

The grapes were then turned into wine in cellars and the dry white wines obtained after chaptalization were found, by analysis, to have the following properties:

TABLE V

| | Alcohol % by volume | Total acidity g/l H$_2$SO$_4$ |
| --- | --- | --- |
| Control Sauvignon | 12.5 | 5.6 |
| Treated Sauvignon | 12.9 | 4.8 |

This Table V reveals that the treatment by the process according to the invention has the effect of somewhat reducing the total acidity of the wine, which in this case, is a dry white wine.

This reduction in acidity is considered as favourable with respect to the organoleptic characteristics of the wine and contrasts with the increase in acidity observed in sweet wines (Test No. 1).

Tests No. 3

Tests were carried out on plots containing 6,600 stocks per hectare of Gamay and Cabernet Franc vines. The above-mentioned composition was atomised on to manually stripped vines at a rate of 40 liters per hectare. The following Table shows the date of treatment and harvesting of the different vines. (Tests carried out by the Lycée Viticole D'Amboise).

TABLE VI

| Vines | Date of Treatment | Date of Harvest |
| --- | --- | --- |
| Gamay | 26/9/86 | 7/10/86 |
| Carbernet Franc | 10/10/86 | 21/10/86 |

Analysis of the control and treated grapes produced the results shown in Table VII below:

TABLE VII

| Vines | Alcohol potential in % by volume | Total acidity in g/l H$_2$SO$_4$ |
| --- | --- | --- |
| Gamay | | |
| Control | 10.7 | 8.8 |
| Treated | 12 | 8.7 |
| Cabernet Franc | | |
| Control | 9.5 | 8.0 |
| Treated | 10.2 | 7.6 |

This Table VII shows that the total acidity of the treated grape must is comparable to that of the untreated grape must, in contrast to what might have been feared, whereas the increase in the potential alcoholometric content is noteworthy.

The grapes were then turned into wine and produced red wines having the following properties, as shown by analysis:

TABLE VIII

| Vines | Alcohol in % by volume | Total acidity | DO280 |
| --- | --- | --- | --- |
| Gamay | | | |
| Control | 10.45 | 2.7 | 0.262 |
| Treated | 11.55 | 2.5 | 0.338 |
| Cabernet Franc | | | |
| Control | 11.5 | 3.2 | 0.32 |
| Treated | 12.30 | 3.2 | 0.364 |

The D0280 was determined by the method described by J. RIBEREAU-GAYON, P. RIBEREAU-GAYON, E. PEYNAUD and P. SUDRAUD in the "Traité d'Oenologie", Sciences et Techniques du Vin, (Dunod), 1972, Volume 1, page 471.

This D0280 index measures the quantity of phenolic compounds present in the wine. These phenolic compounds affect the colour and taste of the wine.

It is considered that the higher the phenolic compound content of a red wine, the better its organoleptic properties.

Table VIII shows an unexpected increase in the D0280 index of wines obtained from grapes treated by the process according to the present invention.

This increase in the D0280 index is accompanied by a significant increase in the alcohol content of the wines, without significant modification of their total acidity.

Tests No. 4

These tests were carried out in 1986 on the estate of "La Tour Blanche" in Bommes, Langon (France) on plots containing 2,800 stocks of Merlot vines per hectare.

The above-mentioned composition was atomised at a rate of 20 liters and 40 liters per hectare. The following Table shows the dates of treatment and harvest:

TABLE IX

| Quantity Sprayed Liter/Hectare | Date of treatment | Date of harvest |
| --- | --- | --- |
| 20 | 1/10/86 | 11/10/86 |
| 40 | 1/10/86 | 11/10/86 |

Analysis of the control and treated grapes gave the results shown in following Table:

TABLE X

| | Alcohol potential in % by volume | Total acidity in g/l H$_2$SO$_4$ |
| --- | --- | --- |
| Control Merlot | 9.9 | 4.9 |
| Treated with 20 l/ha | 10.1 | 4.9 |
| Treated with 40 l/ha | 10.55 | 4.6 |

This table demonstrates that the significant increase in the alcoholometric content has not caused an increase in the total acidity of the must from the treated grapes.

The grapes were then turned into wine and produced red wines which were found, by analysis, to have the following properties:

TABLE XI

| | Alcohol in % by volume | Total acidity in g/l H$_2$SO$_4$ | DO280 | I.F.C. |
| --- | --- | --- | --- | --- |
| Control | 10.61 | 2.8 | 0.314 | 0.691 |

TABLE XI-continued

| | Alcohol in % by volume | Total acidity in g/l H₂SO₄ | DO280 | I.F.C. |
|---|---|---|---|---|
| Merlot Treated with 20 l/ha | 11.30 | 2.8 | 0.35 | 0.918 |
| Treated with 40 l/ha | 11.90 | 3.1 | 0.372 | 0.937 |

Table XI shows the following beneficial effects of the treatment of Merlot vines from "La Tour Blanche":

The red wines obtained from treated grapes had a phenolic compound content (values of D0280 index) which is surprisingly higher than that of wines originating from untreated grapes;

The IFC-index of colouration (determined by the Sudraud-Glories method "La couleur des vins rouges, connaissance de la vigne et du vin", No. 4, 1984, Y. Glories) which measures the sum of occurences of red, yellow and blue in the colour of the wine, is shown to be clearly better than that of wine originating from untreated grapes;

The alcohol content of the wine originating from treated grapes is also clearly better than that of the wine obtained from untreated grapes whereas the acidity of these wines remains comparable.

A person skilled in the art could not have anticipated these effects, in particular the significant increase in the D0280 and IFC indices.

From the following table where tests Nos. 3 and 4 are compared, it appears that the increase of the D0280 index and the IFC index is always greater than the increase of the alcohol content.

TABLE XII

| | % alcohol | | DO280 | | I.F.C. | |
|---|---|---|---|---|---|---|
| | untreated | treated Δ % | untreated | treated Δ % | untreated | treated Δ % |
| Test 3 | | | | | | |
| Gamay | 10.45 | 11.55 + 10.5 | 0.262 | 0.338 + 29 | | |
| Cabernet | 11.5 | 12.3 + 7.0 | 0.32 | 0.364 + 13.8 | | |
| Test 4 | | | | | | |
| Merlot | 10.61 | 11.30 + 6.5 | 0.314 | 0.35 + 11.5 | 0.691 | 0.918 + 32.9 |
| | 10.61 | 11.90 + 12.2 | 0.314 | 0.372 + 18.5 | 0.691 | 0.937 + 35.6 |

The process according to the invention does not only dehydrate the grapes but modify the ratio of the grapes various constituents. The wine growner was not able to predict that it was possible to modify the ratio of the grapes various constituents so as to improve the organoleptic properties of the wine.

Tests No. 5

These tests were carried out in 1986 on the estate of Mr. Roy at Chorey-les-Beaunes (France) on plots of Pinot Noir. The treatment at a rate of 40 liters per hectare was carried out 12 days before the harvest (30 Sept. 1986).

The must from the treated grapes had an alcoholometric content of 11% by volume and a total acidity of 6.3 g/l H₂SO₄, corresponding to an increase of 19.6% in the alcoholometric content and a reduction of 13.7% in the total acidity relative to the alcoholometric content and the total acidity of the must from untreated grapes, the inexplicable reduction in the total acidity being considered as beneficial to grapes from the Pinot Noir Stock.

After wine production, the wine obtained from treated grapes was more highly coloured and contained more phenolic compounds than the wine obtained from untreated grapes. The D0280 index for the wine obtained from treated grapes was 7% better than that of the wine obtained from untreated grapes and the IFC index of the wine from treated grapes was 33% better than that of wine from untreated grapes.

Tests No. 6

(Institut des Techniques du Vin de Nimes)

In view to test the action of the above composition when used to replace standard fungicidal products used at stage D of standard treatment.

Fungicidal products were Romilan ® and Silbas DF ® which were applied following the standard application thereof.

Four plots were tested.

In plot No. 1, the fungicidal reference products were applied at stages A, B, C and D.

In plot No. 2, fungicidal reference products were applied at stages A, B, C and D and the above composition was applied 8 days before harvest.

In plot No. 3, fungicidal reference products were applied at stages A, B and C and the above composition was applied at stage D.

In plot No. 4, fungicidal reference products were applied at stages A, B and C and the above composition was applied at stage D and 8 days before harvest.

The results of these tests are given in the following Table:

TABLE XIII

| | Alcohol potential | |
|---|---|---|
| | Check on ripeness 3 days before harvest | On must at harvest |
| Plot No. | | |
| 1 | 11.0° GL | 10.8° GL |
| 2 | 11.6° GL | 12.1° GL |
| 3 | 11.1° GL | 11.3° GL |
| 4 | 10.7° GL | 10.8° GL |

From these tests, it appears that single application 8 to 10 days before harvest was preferable.

An earlier application (at stage D) did not provide better results.

For grapes of each plot, small-scale vinification was carried out. The vines obtained from plots 2 and 4 were preferred on tasting.

Tests No. 7

(Institut des Techniques du Vin de Colmar)

These tests were conducted by the ITV COLMAR in order to observe the action of the above composition on the development of Botrytis.

Five plots were treated as follow:

Plot 1

Treatment with SILBOS DF at the rate of 5 kg/ha at stages B, C and D and treatment with the above composition (see page 7) at the rate of 25 l/ha 8 days before harvest.

Plot 2

Treatment with SILBOS DF at the rate of 5 kg/ha at stages B and C and treatment with the above composition (25 l/ha) at stage D.

Plot 3

Treatment with SILBOS DF (5 kg/ha) at stages B and C and treatment with the above composition (25 /ha) at stage D and 8 days before harvest.

Plot 4

Treatment with SILBOS DF (5 kg/ha) at stages B, C and D.

Plot 5

No treatment.

The action on Botrytis expressed by the average % of grapes affected is given in the following Table:

TABLE XIV

|  | Average % grapes affected | Average effectiveness |
|---|---|---|
| Plot 1 | 7.2 | 62 |
| Plot 2 | 12.7 | 32 |
| Plot 3 | 11.2 | 40 |
| Plot 4 | 10 | 47 |
| Plot 5 | 18.7 |  |

It appears from this table that the process according to the invention gives the better results when the above composition is applied 8 days before harvest for vine treated at stage B, C and D with SILBOS.

The action of the above composition has also been studied on bunches with peduncular rot which appears on the grapes of plots 1 to 5.

TABLE XV

|  | Average % of peduncular rot | Average effectiveness (%) |
|---|---|---|
| Plot 1 | 2 | 81 |
| Plot 2 | 4.5 | 57 |
| Plot 3 | 1.5 | 86 |
| Plot 4 | 5 | 47 |
| Plot 5 | 10.5 | — |

This table shows that a late treatment with the above composition 8 days before harvest gives the best results.

The above composition contains a preponderant amount of ethyl oleate. Tests made on wine from treated grapes and on wine from untreated grapes have shown that the ethyl oleate content was in both wines less than 0.5 mg/l, i.e. the treatment of grapes with the above composition leaves no ethyl oleate residues in wine.

The process for the treatment of grapes intended for wine production according to the invention allows the alcoholometric content of the grapes to be increased and therefore necessitates no or far slighter chaptalization of the wine.

The quantities required of the composition to be used according to the invention can vary between 5 and 50 liters per hectare, this quantity being a function of the vine, the degree of maturity of the grape, the type of bloom, the climate and the nature of the soil, etc.

The compositions used according to the invention also have a fungistatic effect in the sense that they allow decay of the grapes to be stabilised, that is to say they allow the growth of the *Botrytis cinerea* to be stabilised. *Botrytis cinerea* has a beneficial effect on the production of liqueur-type or sweet white wine and an undesirable and unpleasant effect on red wines and dry white wines. This stabilisation of the growth of Botrytis allows slightly more acid wines to be obtained for liqueur-type white wines, as this is preferable for this type of wine, and allows less acidic dry white wines and red wines, which is also desirable for the taste of these wines.

As seen above, the process according to the invention allows not only a substantial increase in the alcohol content of the wines, while increasing their total acidity in the case of liqueur-type or sweet white wines and while maintaining or reducing somewhat their total acidity in the case of red wines and dry white wines.

The process according to the invention also allows a surprising improvement in the organoleptic properties (D0280 and IFC indices) of the red wines.

Wines providing from grapes harvested in 1986 were tested by twelve professional tasters at the Oenological Institute of the University of Bordeaux in March 1987.

Each taster gave a cotation for wines obtained from treated grapes and from untreated grapes.

A summary of the tasting on said wines is given hereafter:

AMBOISE - white wines

Control Sauvignon: 11.4/20

Pale yellow, clear wine, fairly heavy aroma not very characteristic of Sauvignon. Acidity dominating in the mouth. A simple light wine.

Treated Sauvignon: 13.3/20

Slightly yellower. More marked Sauvignon character, more aromatic. Although the acidity is marked, it is softer and fuller in the mouth. A more complex wine.

TOUR BLANCHE - white liqueur-like wines

Harvest without selection

Control Sémillon: 10.7/20

Greeny yellow colour untypical of a Sauterne, simple bouquet low in character. Not very soft or full to the taste.

Treated Sémillon: 14.8/20

Stronger golden yellow colour more inkeeping with Sauternes wines, complex fruity bouquet. Typical fruity character of botrytis-infected grapes. Very soft and full to the taste.

Harvest with selection

Control Sémillon: 11.3/20

Paler in colour than the treated wine. Moderate aromatic intensity. Lack of clarity in nose (smell of fungus). Less soft and full in the mouth than the treated wine.

Treated Sémillon: 12.8/20

Good colour for a Sauterne. Aromatic intensity comparable with that of control wine. Fruity bouquet. In the mouth it was considered balanced with a soft, full and mellow taste. Not very characteristic however.

TOUR BLANCHE - red wines

Treatment 10 days before harvest

Control Merlot: 11.7/20

Average colour intensity and aroma. Light but balanced taste structure. Has some finesse.

Merlot treated with 20 l/ha: 12.2/20

Darker in colour, more aromatic but coarser and vegetal. To the taste, it has a good structure, more tannin. but is coarser and vegetal.

Treated Merlot 40 l/ha: 12/20

Comments regarding the preceding treated wine are repeated here, the treated wine appearing richer but less fine than said preceding wine.

AMBOISE

Control Gamay: 8.3/20

Low colour intensity and slight aroma. Little lingering fragrance to the taste, vegetal.

Treated Gamay: 9.3/20

Slightly deeper in colour, slightly more intensely aromatic. Fruitier. Considered pleasanter and better balanced to the taste.

BURGUNDY

Control Pinot: 7.4/20

Light in colour, more neutral nose. Dominant acidity to the taste.

Treated Pinot: 9.0/20

Deeper colour but still mediocre. More aromatic. Fuller and richer to the taste.

What I claim is:

1. A process for improving the organoleptic properties of wines comprising the steps of
treating standing grapes less than one month before harvest with a composition consisting essentially of a surface active-agent formed from a saponification of an oil by means of an alkali metal hydroxide in the presence of an alcohol selected from the group consisting of ethanol and isopropanol to form a saponified oil that renders the cuticle of said grapes hydrophilic;
applying said composition at a rate of 5 to 50 liters per hectare;
harvesting said grapes, and
processing said grapes.

2. A process according to claim 1, in which said alcohol is ethanol.

3. A process according to claim 2, in which said alkali metal hydroxide is KOH.

4. A process according to claim 2, in which said oil comprises 18 carbon atoms.

5. A process according to claim 1, in which said saponified oil is a saponified edible vegetable oil, said oil containing at least one compound selected from the group consisting of an unsaturated fatty acid of at least 16 carbon atoms and an unsaturated alcohol of at least 16 carbon atoms.

6. A process according to claim 5, in which said saponified edible vegetable oil has a degree of saponification between 10 and 70%.

7. A process according to claim 5, in which said saponified edible vegetable oil consists essentially of a compound selected from the group consisting of oleic acid and 9-octadecenol.

8. A process according to claim 5, in which said saponified edible vegetable oil is selected from the group consisting of olive oil, coconut oil, palm oil, safflower oil, soya oil, rapeseed oil, sunflower oil, corn oil, ground-nut oil, almond oil, sesame oil, and grape pip oil.

9. A process according to claim 5, in which said composition consists essentially of 50 to 80 parts by weight of said saponified edible vegetable oil saponified using 5 to 25 parts by weight of potassium hydroxide and 5 to 30 parts by weight of ethanol.

10. A process according to claim 5, in which said saponified edible vegetable oil comprises 18 carbon atoms.

11. A process according to claim 5, in which said saponified edible vegetable oil has a degree of saponification between 20 and 40%.

12. A process according to claim 5, in which
said saponified edible vegetable oil consists essentially of long chain fatty acids; and wherein said alkali metal hydroxide is potassium hydroxide and said alcohol is isopropanol.

13. A process according to claim 5, in which
said edible vegetable oil consists essentially of long chain fatty acids; and wherein said alkali metal hydroxide is potassium hydroxide and said alcohol is ethanol.

14. A process according to claim 5, in which said surface-active agent consists essentially of 60 to 70 parts by weight of said edible vegetable oil saponified using with 10 to 20 parts by weight of potassium hydroxide and 15 to 25 parts by weight of ethanol.

15. A process for improving the organoleptic properties of wines comprising the steps of:
spraying standing grapes during a period of time ranging from 5 to 20 days before harvest with an aqueous suspension containing less than 20 percent by volume of a composition consisting essentially of a surface-active agent formed from a saponification of an oil by means of an alkali metal hydroxide in the presence of an alcohol selected from the group consisting of ethanol and isopropanol, to form a saponified oil that renders the cuticle of said grapes hydrophilic;
applying said composition at a rate of 5 to 50 liters per hectare;
harvesting said grapes, and
processing said grapes.

16. A process according to claim 15, in which said saponified oil is a saponified edible vegetable oil, said oil containing at least one compound selected from the group consisting of an unsaturated fatty acid of at least 16 carbon atoms and an unsaturated alcohol of at least 16 carbon atoms.

17. A process according to claim 15, in which said alcohol is ethanol.

18. A process according to claim 17, in which the alkali metal hydroxide is KOH.

* * * * *